US00PP21496P2

(12) United States Plant Patent
O'Connell

(10) Patent No.: US PP21,496 P2
(45) Date of Patent: Nov. 16, 2010

(54) ***ECHEVERIA* PLANT NAMED 'CRIMSON TIDE'**

(50) Latin Name: ***Echeveria* hybrid**
Varietal Denomination: Crimson Tide

(76) Inventor: Renee O'Connell, 1801 Tierra Libertia, Escondido, CA (US) 92026

( * ) Notice: Subject to any disclaimer, the term of this patent is extended or adjusted under 35 U.S.C. 154(b) by 0 days.

(21) Appl. No.: 12/455,707

(22) Filed: Jun. 6, 2009

(51) Int. Cl.
*A01H 5/00* (2006.01)

(52) U.S. Cl. ..... Plt./372
(58) Field of Classification Search ..... Plt./372

See application file for complete search history.

*Primary Examiner*—Annette H Para

(57) ABSTRACT

A new and distinct *Echeveria* cultivar named 'Crimson Tide' is disclosed, characterized unique vividly colored leaf margins which are unusually undulating and thick. Leaf margins are also distinctively anfractuous. The new variety is an *Echeveria*, typically produced as a garden or container plant.

1 Drawing Sheet

Figure 1:
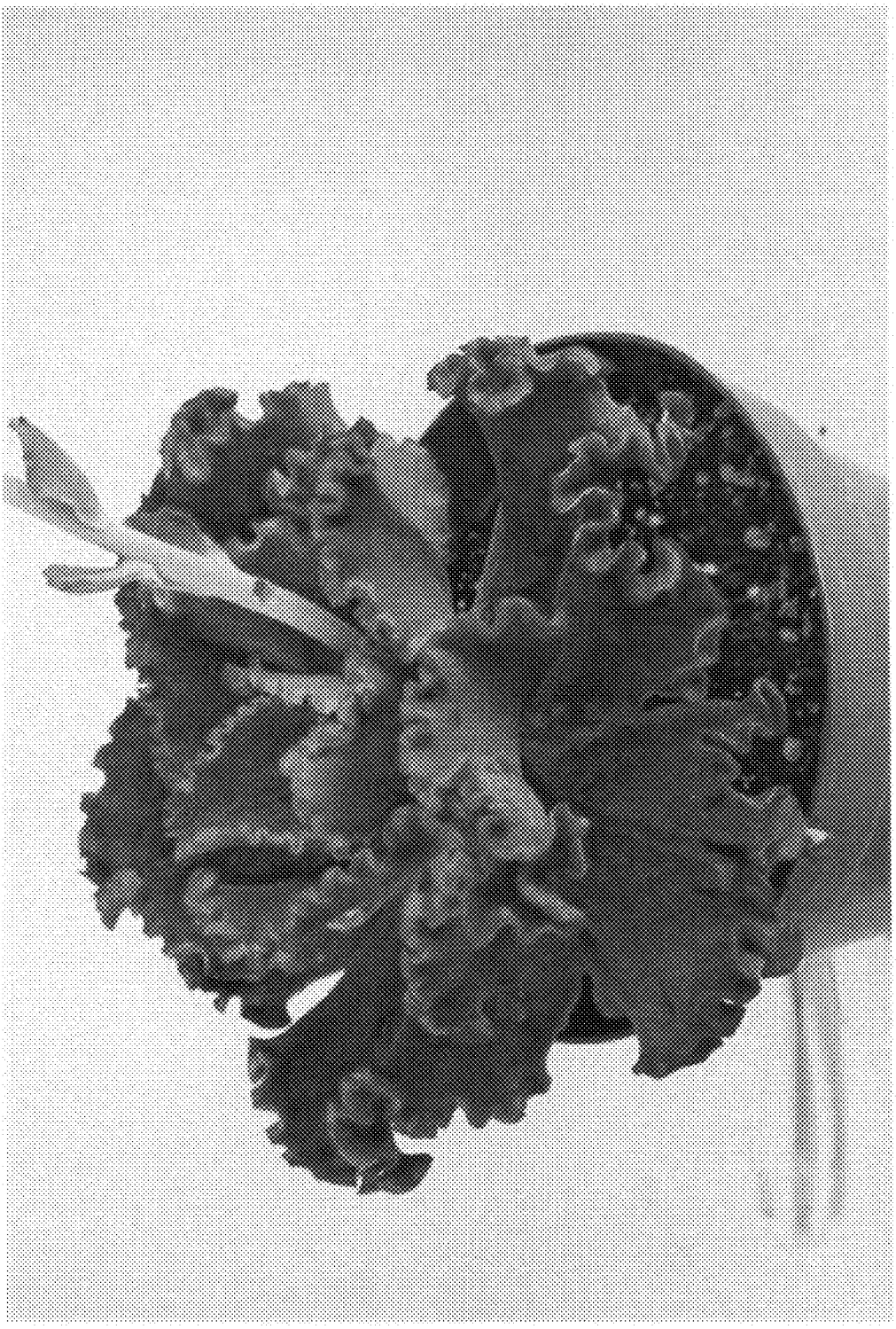

Latin name of the genus and species: *Echeveria* hybrid.
Variety denomination: 'Crimson Tide'.

BACKGROUND OF THE INVENTION

The new cultivar is a product of a planned breeding program. The new variety originated from a cross pollination of the unpatented, proprietary seed parent, *Echeveria* hybrid referred to as '#26' with the pollen parent an unpatented proprietary *Echeveria* hybrid referred to as 'Big Red.' The crossing was made during October of 2005 in Vista, Calif., at a commercial greenhouse. 'Crimson Tide' was discovered by the inventor, Renee O'Connell, in February 2007, in Vista, Calif. at a commercial greenhouse.

Asexual reproduction of the new cultivar 'Crimson Tide' was first performed in Vista, Calif., at a commercial greenhouse by vegetative leaf cuttings in February 2007. 'Crimson Tide' has since produced several generations and has shown that the unique features of this cultivar are stable and reproduced true to type.

SUMMARY OF THE INVENTION

The cultivar 'Crimson Tide' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Crimson Tide.' These characteristics in combination distinguish 'Crimson Tide' as a new and distinct *Echeveria* cultivar:

1. Unique vividly colored leaf margins.
2. Unusual undulating, thick leaf margins.
3. Distinctive anfractuous leaf margins.

PARENTAL COMPARISON

Plants of the new cultivar 'Crimson Tide' are similar to the seed parent '#26' in most horticultural characteristics. However, 'Crimson Tide' exhibits unusual brightly colored, anfractuous leaf margins not seen on the seed parent. Additionally, 'Crimson Tide' grows faster, and shows an overall better resistance to normal diseases and pests of *Echeveria* than the seed parent.

Plants of the new cultivar 'Crimson Tide' are similar to the pollen parent 'Big Red' in most horticultural characteristics. However, 'Crimson Tide' exhibits more undulating, brighter colored leaf margins than the pollen parent. Additionally, 'Crimson Tide' has an overall shorter, more compact plant morphology than 'Big Red.'

COMMERCIAL COMPARISON

'Crimson Tide' can be compared to the unpatented commercial variety *Echeveria* 'Strawberry Hearts.' Plants of *Echeveria* 'Strawberry Hearts' are similar to plants of 'Crimson Tide' in most horticultural characteristics. However, 'Crimson Tide' does not grow as tall as 'Strawberry Hearts' and produces a more irregular rosette plant form. Additionally, plants of 'Crimson Tide' produce a more anfractuous leaf margin than 'Strawberry Hearts.'

'Crimson Tide' can also be compared to the unpatented commercial variety *Echeveria* 'Arlie Wright.' Plants of *Echeveria* 'Arlie Wright' are similar to plants of 'Crimson Tide' in most horticultural characteristics. However, 'Crimson Tide' is a shorter plant, which exhibits more resistance to the disease powdery mildew than 'Arlie Wright.' Additionally, the foliage of 'Crimson Tide' has a more intense margin color, and a more undulating, anfractuous form.

BRIEF DESCRIPTION OF THE PHOTOGRAPH

The accompanying photograph in FIG. 1 illustrates in full color a typical plant of 'Crimson Tide' grown outdoors in Vista, Calif. This plant is approximately 9 months old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to the Pantone Process Color System Guide, except where general terms of ordinary dictionary significance are used. The following observations and measurements describe 'Crimson Tide' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.
Botanical classification: *Echeveria* hybrid 'Crimson Tide.'
Age of the plant described: Approximately 5 months.

PROPAGATION

Time to initiate roots: About 25 days at approximately 21° C.
Root description: Fibrous.
Propagation method: Vegetative divisions, leaf cuttings.

PLANT

Growth habit: Rosulate plant, sessile, rarely branching.
Container size: 6 inch.
Height: Approximately 15 cm to top of highest leaf.
Plant spread: Approximately 19 cm.
Growth rate: Slow-moderate.
Branching characteristics: Rarely.

FOLIAGE

Leaf:

*Arrangement.*—Rosulate; sessile.
*Average length.*—Approximately 11 cm.
*Widest width.*—Approximately 8.75 cm.
*Width at base.*—Approximately 2 cm.
*Shape of blade.*—Spatulate.
*Apex.*—Rounded, crenulate.
*Base.*—Rounded.
*Margin.*—Crenulate, anfractuous.
*Texture of top surface.*—Glabrous, pruniose.
*Texture of bottom surface.*—Glabrous; pruinose.
*Quantity of leaves per plant.*—Approximately 20.
*Color.*—Young foliage upper side: Near S 137-5 Pantone. Young foliage under side: Near S 307-9 Pantone. Young foliage margin: Near S 107-8 to S 107-3 Pantone. Mature foliage upper side: Near S 137-6 Pantone. Margin near Near S 107-1 Pantone. Mature foliage under side: Near S 137-6 Pantone. Margin near Near S 107-1 Pantone. Mature foliage, under side; if pruinose covering is removed: Near S 291-8 Pantone. Mature foliage margin: Near S 107-1 Pantone.

Venation:

*Type.*—Parallel.
*Venation color upper side.*—Indistinguishable from overall foliage color.
*Venation color under side.*—Indistinguishable from overall foliage color.

FLOWER

Natural flowering season: Late winter, late autumn.
Flowering: Plants were not flowering at the time the botanical description was made, as all plants of the new variety had flowers removed for propagation purposes.

OTHER CHARACTERISTICS

Fruits and seeds: Not observed to date.
Temperature tolerance: Tolerates temperatures from approximately −2 C to 32 C.
Disease/pest resistance: Neither resistance nor susceptibility to normal diseases and pests of *Echeveria* has been observed.
Drought tolerance: Tolerates at least 2 weeks of high temperatures without supplemental water, showing no serious damage to plant.

What is claimed is:

1. A new and distinct cultivar of *Echeveria* plant named 'Crimson Tide' as herein illustrated and described.

* * * * *